(12) United States Patent
Hara (10) Patent No.: US 11,293,000 B2
(45) Date of Patent: Apr. 5, 2022

(54) STERILE HETEROTROPHIC GROWTH BIOREACTOR

(71) Applicant: Field Energy LLC, West Hartford, CT (US)

(72) Inventor: Hiroaki Hara, West Hartford, CT (US)

(73) Assignee: Field Energy LLC, West Hartford, CT (US)

( * ) Notice: Subject to any disclaimer, the term of this patent is extended or adjusted under 35 U.S.C. 154(b) by 113 days.

(21) Appl. No.: 16/345,379

(22) PCT Filed: Oct. 27, 2017

(86) PCT No.: PCT/US2017/058728
§ 371 (c)(1),
(2) Date: Apr. 26, 2019

(87) PCT Pub. No.: WO2018/081539
PCT Pub. Date: May 3, 2018

(65) Prior Publication Data
US 2019/0264152 A1    Aug. 29, 2019

Related U.S. Application Data

(60) Provisional application No. 62/413,663, filed on Oct. 27, 2016.

(51) Int. Cl.
| C12M 1/00 | (2006.01) |
| C12N 1/12 | (2006.01) |
| C12M 1/04 | (2006.01) |
| C12M 1/12 | (2006.01) |
| B01F 3/04 | (2006.01) |

(52) U.S. Cl.
CPC ......... *C12M 23/14* (2013.01); *B01F 3/04106* (2013.01); *C12M 1/00* (2013.01); *C12M 1/04* (2013.01); *C12M 1/12* (2013.01); *C12M 21/02* (2013.01); *C12M 23/20* (2013.01); *C12N 1/12* (2013.01)

(58) Field of Classification Search
None
See application file for complete search history.

(56) References Cited

U.S. PATENT DOCUMENTS

| 5,565,015 A * | 10/1996 | Kobayashi ............. C12M 37/00 71/9 |
| 2009/0305389 A1* | 12/2009 | Willson ................. C12M 21/02 435/257.1 |

(Continued)

FOREIGN PATENT DOCUMENTS

CN     102408983 A * 4/2012    ............ C12M 23/14

*Primary Examiner* — William H. Beisner
(74) *Attorney, Agent, or Firm* — Alix, Yale & Ristas, LLP (57) ABSTRACT

A sterile bioreactor is formed of a combination of a bag and a bubble diffuser retained in the bag. The bubble diffuser is formed of a microporous sheet material that produces substantially uniform micro gas bubbles for enhancing plant organism growth within the bag. The bag is made in a cost-effective manner and with desired sterility by sealing coupling devices and/or ports, the tube ends sealed and gamma irradiated. The coupling devices/ports are established in one side wall of the bag. Contents may be inserted into and removed from the bag through the coupling devices/ports, which may be surface mounted portals.

12 Claims, 4 Drawing Sheets

(56) References Cited

U.S. PATENT DOCUMENTS

2013/0082410 A1\* 4/2013 Goodwin ............... C12M 23/14
    261/42
2014/0322804 A1\* 10/2014 Boily .................... C12M 21/02
    435/292.1

\* cited by examiner

STERILE HETEROTROPHIC GROWTH BIOREACTOR

BACKGROUND OF THE INVENTION

1. Field of the Invention

The present invention relates to reactors used to enable the growth of plant organisms. More particularly, the present invention relates to bioreactors used to facilitate the growth of algae. Still more particularly, the present invention relates to the construct of bioreactor bags suitable for heterotrophic or mixotrophic algae growth.

2. Description of the Prior Art

Algae are the fastest growing plant organisms in nature and are extremely diverse. Algae form the base of the aquatic food chain. They can naturally produce carbohydrates, oils, protein, vitamins and organic minerals that feed crustaceans and up the food chain to fish. Algae can also provide directly nutrients otherwise obtained from fish, including, for example, docosahexaenoic acid (DHA), which is an omega-3 fatty acid naturally found in some species of algae and plankton and often in the food chain in fatty fish used for fish oil. The benefits associated with the use of DHA are well documented. It is therefore becoming an increasingly desirable product directly and as a food supply and/or supplement for fish. It is further noted that, more generally, algae and its constituents including, but not limited to, DHA may be used as a food or supplement source for other animals.

DHA is typically obtained from fish oil. The quality of DHA from fish oil is not consistent because it is dependent on the environment of its food chain. DHA omega-3 produced through algae is a viable alternative to fish oil that can be quickly produced commercially with limited land use and no detectable "fishy" taste in the functional foods sold to consumers. It is therefore desirable to increase the production of algae as a direct source of DHA, an indirect source of DHA through sustainable farming of fish and land animals, and using the algae as a diet component feed. Enhancement of algae growth is desirable for the purpose of generating a food and/or supplement source for other purposes not limited to DHA production.

The interest in increasing and optimizing the growth of algae has spurred the development of bioreactors and methods directed to plant organism growth, including algae growth. There are three mechanisms of growth, namely, autotrophic, heterotrophic and mixotrophic. Autotrophic growth occurs when microalgae are exposed to sunlight, carbon dioxide and some nutrients and the resultant combination produces an algae biomass. Unfortunately, the blockage of sunlight penetration limits the algae's ability to grow beyond certain culture density. Alternatively, heterotrophic growth does not require sunlight to produce the algae biomass; instead, an oxygen source and nutrients combine with the microalgae to produce the biomass. This form of production has advantages in large scale production as growth can occur in smaller space than is needed for autotrophic growth and without the need for access to sunlight. It is desirable to provide an effective mechanism for heterotrophic growth of algae that is economically feasible to employ.

One fairly cost-effective device for autotrophic algae growth is the SeaCAPS™ system available from Seasalter Shellfish (Whitstable) Ltd of the United Kingdom. The device is a plastic bag retained in place by a wire cage. The bag simply comes on a roll of seamless tube otherwise called lay-flat tube, sealed and perforated at 7-8 feet long like a roll of trash bags, that can be separated from one another at a perforation—much like a set of bags. There is a wedge at the bottom of the cage that is designed to support the bag and balance the pressure of water inside the bag to prevent it from being torn at the seam. The bag can be filled with starter material such as microalgae. A plurality of tubes is inserted into the bag wall to allow for the introduction of water, nutrients, and air, and to allow for the removal of biomass and the venting of exhaust gases from the production process. The tubes are simply inserted by puncturing the bag wall and the bag material self-seals about the perimeters of the tubes by the pressure of water inside. While that is sufficient for reasonably satisfactory autotrophic algae growth, it is not sufficient for heterotrophic growth, which requires greater sterility than is available using the SeaCAPS™ bag. Therefore, what is needed is a biomass growth container with satisfactory sterility for heterotrophic growth.

It is important in facilitating effective algae growth to introduce enough oxygen, generally by way of an air source. In particular, it is understood that optimal dissolved oxygen content within the container increases biomass yield and, as a result, lipid and DHA yield if that is a desired output from the bioreactor that is comprised of the container, its contents and the mechanisms employed to introduce nutrients and oxygen, and to output product and exhaust gases.

Aerobic fermenters or aerobic fermentation bioreactors haves been the equipment of choice in heterotrophic cultivation of algae or other microorganisms in the past. It is generally a rigid cylindrical structure made with glass, rigid plastic, or stainless steel. The introduction of air or oxygen is facilitated by incorporation of a coaxially located impeller that stirs in bubbles in order to increase the gas exchange contact surface area within the reactor. Generally, the impeller extends from a shaft that supports the impeller. Magnetic stirrers may be used instead of or in addition to the impeller with shaft. This type of equipment is rather expensive and is associated with costly maintenance. Further, in order to maximize the desired gas exchange surface area, the rotation of the impeller must be very fast and so is therefore highly energy consuming and, correspondingly, expensive and potentially cell damaging.

The introduction of nanometer-sized air/oxygen bubbles is an alternative, more passive, attempt to enhance the dissolved oxygen content of the fluid within the bioreactor. However, such a bubble size ends up being disadvantageous because the bubble is so small it does not float up, rather it is suspended in liquid with "Brownian motion." Thus, when the biomass density increases, its oxygen consumption is maximized, and especially when atmospheric air is used as the oxygen source, all of the oxygen introduced is quickly converted to carbon dioxide during biomass formation. At the same time, suspended small bubbles in the mix do not float up quickly enough to be replaced by fresh bubbles, thereby choking the biomass and limiting optimal growth. Gas bubble disease, an impediment to high yield, high quality, algae biomass growth, is mainly the result of oxygen deficiency in the container. Optimal bubble size for continuous supply of oxygen is therefore micron-size bubbles with continual flow of coalesced macro bubbles. Diffusers have also been employed to reduce the size of introduced gas bubbles. The greater the number of pores of the diffuser; i.e., the greater the diffuser's surface area, a larger number of bubbles can be generated at given air flow rate for a higher gas exchange surface area at given time. However, the diffusers available for present bioreactors of the type of the present invention have been primarily solid sintered tubes or plates that are difficult to secure to the bottom of the reactor, due to its buoyancy when filled with air. These diffusers are also relatively much more expensive to produce. What is needed is an effective bioreactor for suitable heterotrophic algae growth at optimal yield in a cost-effective way.

SUMMARY OF THE INVENTION

The present invention is a sterile heterotrophic algae growth bioreactor. It can also be used for mixotrophic growth, because the outer film is translucent, and while in use, the microbubbles inside will act as a reflector/refractor to let the light to effectively penetrate deeper into otherwise opaque layer of biomass. The bioreactor is a container in the form of a plastic reactor bag. The bag is formed of a plastic material with sufficient thickness and toughness to retain the contents suitable for algae biomass production without failing and while limiting or preventing bacterial contamination. The bag includes coupling devices or coupling ports for introduction and removal of bag contents. The coupling devices or ports are located on one wall of the bag. The bag may be formed of one or more sheets of material dependent on desired thickness and the toughness to resist tearing desired for the reactor. The sheet or sheets of material may be selected to form a bag that is capable of retaining 300 or more liters of fluid, including at least 500 liters of fluid, but is not limited thereto. The bag may be made of polyethylene, nylon, or combinations thereof as bilayer or trilayer configurations thereof but is not so limited; that is, other materials may be employed. The bioreactor, with tubes assembled after fabrication and the sealing or plugging of all tube ends, is gamma irradiated to eliminate possible bio-organism intrusion during the assembly.

The bag may be formed by starting with a sheet of material of selectable dimensions, folding it in half and sealing it at the perimeter seams at a top, or the one side. Alternatively, two sheets of material of substantially equal dimensions may be paired up and sealed at their adjacent perimeters. Installation of the coupling devices at the time of bag formation eliminates the need to pierce the bag wall to insert tubes at the installation site. That improves the sealing of the bag over prior bioreactor bags against bacteria invasion. The bag in which all coupling devices or ports on one side wall of the bag is accomplished by positioning all such devices/ports on one side of the bag, and then heat sealing them in place prior to sealing the bag. By having all of the ports on one side and not the other improves handling of the sheet or sheets of material when making the bag for enclosure sealing.

The number of coupling devices and/or ports sealed at the seams of the bag is selectable. There may be all coupling devices, all coupling ports or a combination of the two. There may be one or more coupling devices/ports for insertion of contents such as fluids, nutrients, inoculant or other materials of choice. There may be one or more coupling devices/ports for insertion of oxygen, such as pure oxygen or air that contains oxygen. Such coupling/ports are further connected inside to the aeration pillows heat sealed into the bottom seam. There may be one or more coupling devices/ports for removal of product and there may be one or more coupling devices/ports for removal of off-gases produced during the biological reaction to make the algae biomass. It is to be understood that when reference is made to the top, the bottom and the side of the bag, that is when the bag is oriented for use, with the top being above the bottom and the side intermediate between the top and the bottom. In such an orientation, contents may be input at the top and/or side of the bag, product may be removed from near the bottom, oxygen may be sourced at the bag near the bottom, and off gases may be removed at the top and/or side of the bag near the top.

In the version with coupling devices/ports located on one bag wall, the coupling device/port may be a surface mount port placed over/through a punctured hole and heat sealed onto the surface of the bag wall of one sheet of material when two sheets of material are used to make the bag. When the bag is made of only one sheet of material, the surface mount ports may be sealed in place on one half of the sheet of material, which is then folded over to form the bag, thereby it is convenient when the final outside seal is made.

Another feature of the bioreactor of the present invention is the component for effectively diffusing oxygen into the contents of the bag. The component is a bubble diffuser that is fixed in the interior of the bag. The bubble diffuser, which may also be referred to as a pillow, is positioned in a lower region of the interior of the bag. Preferably it should be located at the interior bottom of the bag. It is arranged so that a supply of oxygen, such as from air, is directed into the bubble diffuser (pillow) wherein it is diffused through the bubble diffuser to form micro gas bubbles of substantially uniform sizes that pass through the wall of the bubble diffuser to enter a region of the interior of the bag within which contents react with the oxygen of the gas bubbles to provide oxygen to the algae biomass. Some bubbles may coalesce through the migration of floatation to form relatively larger bubbles. These larger macro bubbles are beneficial since they act as an intermediary between relatively slow-moving micro bubbles in terms of oxygen transfer. The bubble diffuser is of selectable size and dimensions. In an embodiment, the bubble diffuser covers substantially large portion of the interior bottom region of the bag. The bubble diffuser is made of a material capable of maintaining its integrity in the reaction environment, that allows for micro bubble diffusion and that is resistant to bacterial growth. The bubble diffuser may be made of Tyvek® or other material that is relatively lightweight sheet and can be heat sealed into the seam of the bag. The Tyvek® material has a microporous surface that generally allows air to pass through. The bubble diffuser is arranged to enable the generation of micron-sized bubbles and, thereby, maximizes the effective gas exchange surface area in the reactor by microbubble introduction. The bubbles introduce oxygen into the liquid culture to be dissolved and to be exchanged with carbon dioxide produced by the biomass. The coalesced macro bubbles are large enough to push through to the head surface of the culture and ultimately to be exhausted from the bag through the exhaust. That is, the bubble size is small enough to accomplish that desired gas exchange but coalesces to large enough bubble to move toward the upper surface of the liquid culture. The constant supply of micro bubbles from the bubble diffuser ensures that sufficient oxygen is supplied to biomass as the contents of the bag thicken with the advancement of the algae production.

The bubble diffuser may be made from one sheet of Tyvek® material of about 7.5 mil thickness, folded and heat-sealed at the bottom seam of the bag, although other sheet thicknesses are possible. Prior to sealing all sides of the bag, a coupling device or coupling port is inserted on the wall of the bubble diffuser from the air inlet port near the bottom of the outer bag with similar heat sealing method. At least one such coupling port is connected through an outer wall of the bag and a wall of the bubble diffuser to form a gas insertion port. Other coupling or couplings is/are established through the outer bag wall only to form a harvesting culture out-port. The bubble diffuser of this type should be primed slowly by gently flowing air through the bubble diffuser prior to major gas injection. In this way, the integrity of the wall structure of the microporous bubble diffuser is maintained and the pore size remains relatively the same rather than being expanded to an undesirable size that can result in an undesirable increase in the size of bubbles exiting the bubble diffuser.

As noted, the bag is preferably gamma irradiated after fabrication, including after incorporation of any tubing at the coupling devices/ports and after tube ends have been sealed to provide complete sterility. In one embodiment of the invention, the bag may have a gusseted bottom and the bubble diffuser is seamed at the outer wall thereof and at the bottom, front and back, of the wall. In another embodiment of the invention, the bag is supported on a wedge to reduce stress on the bag when in use. The bag may be retained in a retaining structure as described herein. It is also noted that an embodiment of the invention provides a sterile bioreactor comprising a plastic bag having a first side wall and a second side wall and one or more seams establishing an interior of the bag, a plurality of coupling devices/ports joined to the bag for the insertion and removal of contents into and out of the interior of the bag, and a bubble diffuser retained in the interior of the bag joined to the bottom seam of the bag, wherein the bubble diffuser is configured to diffuse gas into the interior of the bag to facilitate the growth of plant organisms therein, wherein at least one of the coupling devices/ports is joined to the bag at or near the bottom of the bag to provide gas to the bubble diffuser. In another embodiment, the invention provides a sterile algal bioreactor made with sealed plastic bag with capacity of at least 400 liter per bag, with at least three, and no more than seven tubes connected into it, and at least one and no more than four of such tubes is connected into one or more internal gas dispersing closed end bag that is made of microporous plastic, and such microporous bag has total apparent surface area larger than at least a third of the area of the cross section of such bioreactor, but not exceeding twice the surface area of the cross section of the bioreactor.

The heterotrophic algae growth bioreactor of the present invention is of a sterile configuration. It is made in a cost-effective way. It enables effective distribution of micro bubbles throughout its contents. The result is a high yield, high quality product that is obtained with a bioreactor that is relatively inexpensive. It may be used for growing other plant organisms not limited to algae. These and other advantages of the present invention will become more apparent to one skilled in the art based on the following detailed description, accompanying drawings and appended claims.

DETAILED DESCRIPTION OF THE INVENTION

A bioreactor 10 of the present invention is shown in FIGS. 1-4. The bioreactor 10 includes a bag 12 and a bubble diffuser 14. The bag 12 includes a top 16, a seamed side 18 and a bottom 20. The top 16 and the bottom 20 are also seamed. The top 16 of the bag 12 is that part of the bag 12 that is above the bottom 20 when the bag 12 is oriented as shown such that gas would flow from the bottom 20 toward the top 16. The bag 12 may be made of polyethylene, nylon or combinations thereof as well as other materials having suitable functional characteristics. The back side 18 includes side seam 24 and the bottom includes bottom seam 26, wherein the side seam 24 extends to the bottom 20 of the bag 12 to become the bottom seam 26. The seams 24 and 26 may be made by sealing in an overlapping manner edges of the bag 12. Side 28 is not seamed as it is established by folding the bag 12 in half so that edges of the top 16, the side 18 and the bottom 20 are positioned together. In an alternative embodiment, the bag 12 may be formed by joining two sheets of material together and sealing it on its perimeter, including the formation of a seam at side 28.

Figure 1:
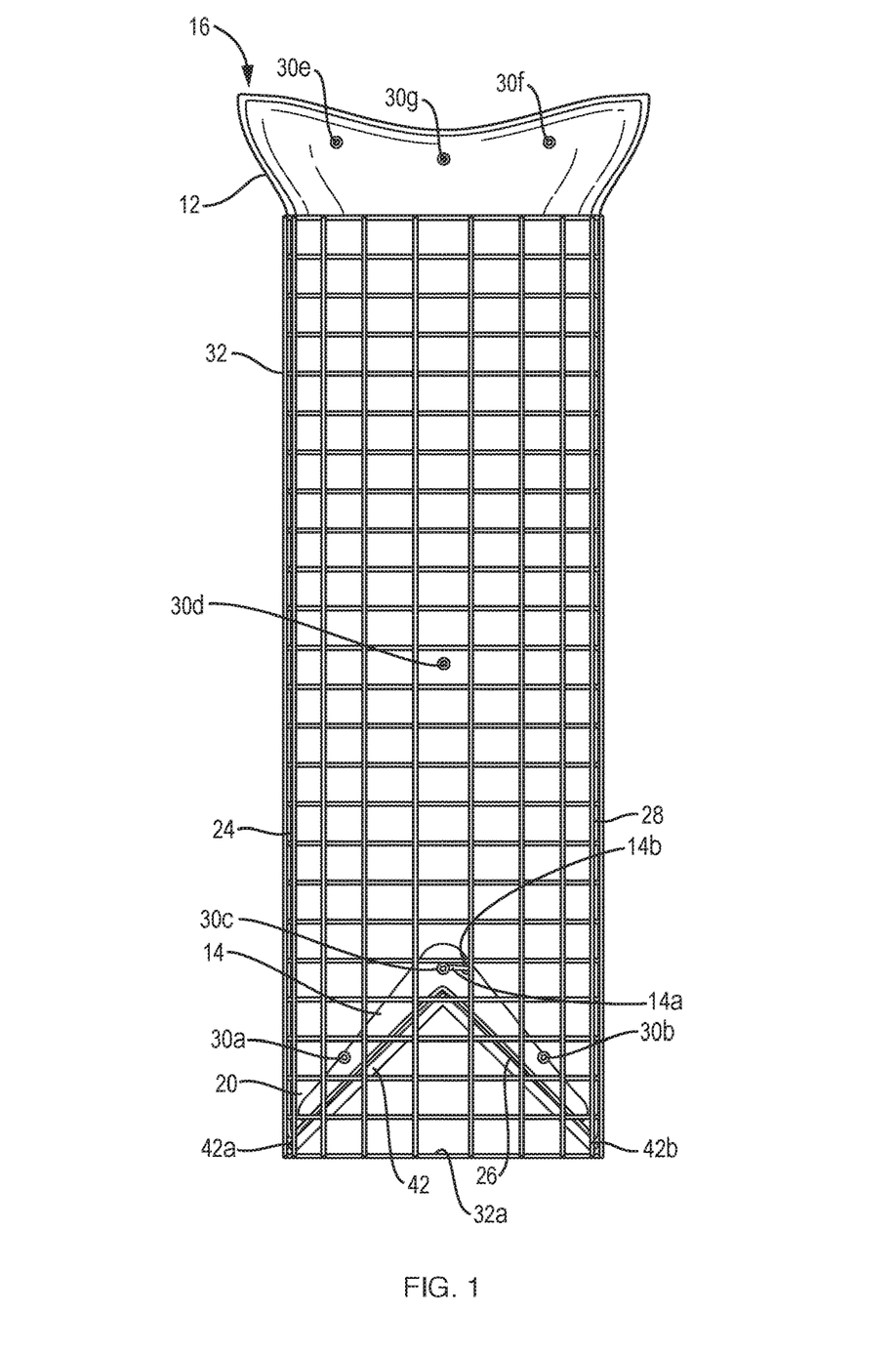
FIG. 1 is a front view of the heterotrophic bioreactor of the present invention.
Figure 2:
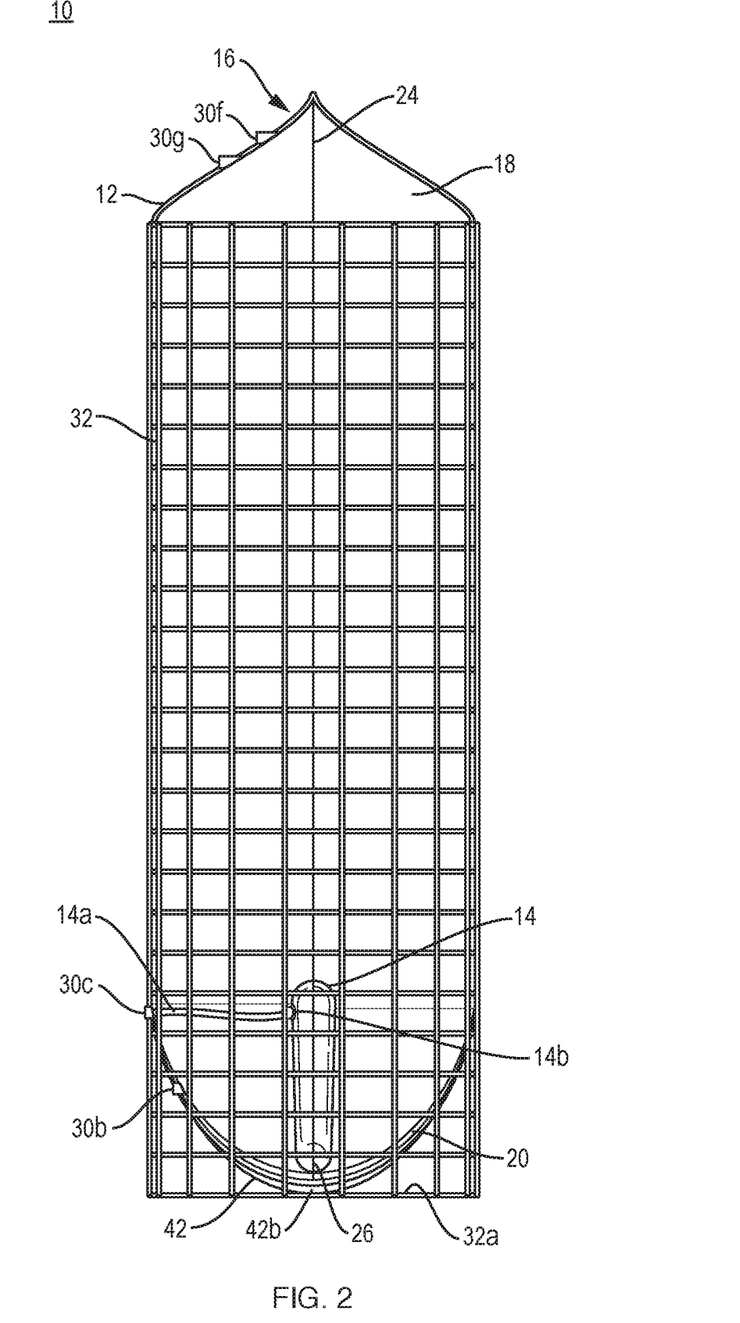
FIG. 2 is a side view of the heterotrophic bioreactor of the present invention.

There are at least four sterile coupling devices and/or coupling ports sealed at the bag 12 so that supply may be added to the interior of the bag 12, air may be directed into the bubble diffuser 14 through internal tube 14*a*, product may be removed from the interior of the bag 12 and off-gasses may be removed from the interior of the bag 12. As illustrated in the representative version of the invention shown in the drawings, there are a total of seven coupling ports represented, including two product outlet ports 30*a* and 30*b*, an air inlet port 30*c* is connected to the diffuser port 14*b* inside the bag with a tube, a sampling outlet port 30*d*, two supply inlet ports 30*e* and 30*f*, and offgas outlet port 30*g*. The coupling devices/ports 30 may be positioned at selectable positions on the bag 12 provided they are located where they function as intended. For example, as shown in FIG. 1, the product outlet ports 30*a* and 30*b* are located near the bottom 20 of the bag 20, air inlet port 30*c* is located in the vicinity of the bubble diffuser 14, the sampling port 30*d* is roughly centered on the bag 12, and the supply inlet ports 30*e* and 30*f* and the offgas outlet port 30*g* are located near the top 16 of the bag 12. Other combinations of placement of the coupling devices/ports 30 are possible including at side 28 if seamed with the two-sheet version of the bag 12. The coupling devices/ports 30 are selected to provide an interface between a source of something to put into or take out of the bag 12 and the interior of the bag 12. The coupling device/ports 30 have releasable engagements with a conduit to supply sources and/or output receptacles. A surface mounted sealing ring or other portal opening is suitable for a coupling port.

It is noted that the bag 12 is made of a flexible material, such as a nonmetallic material. A bag support 32 may be used to provide structural support to the bag 12 so that it generally remains in an upright position when in use. The bag support 32 may further provide a way to keep the shape of the bag 12 generally uniform when filled with material. When the size of the bag 12 is selected for use to process 20 liters or less of fluid, the bag support 32 may be a container having relatively rigid sidewalls. For example, the bag support may be a 20-L Nalgene™ bottle, which is generally available commercially. When the size of the bag 12 is selected for use to process about 500 liters of fluid, the bag support 32 may be a container such as a cage-like structure as represented in the drawings.

Figure 3:
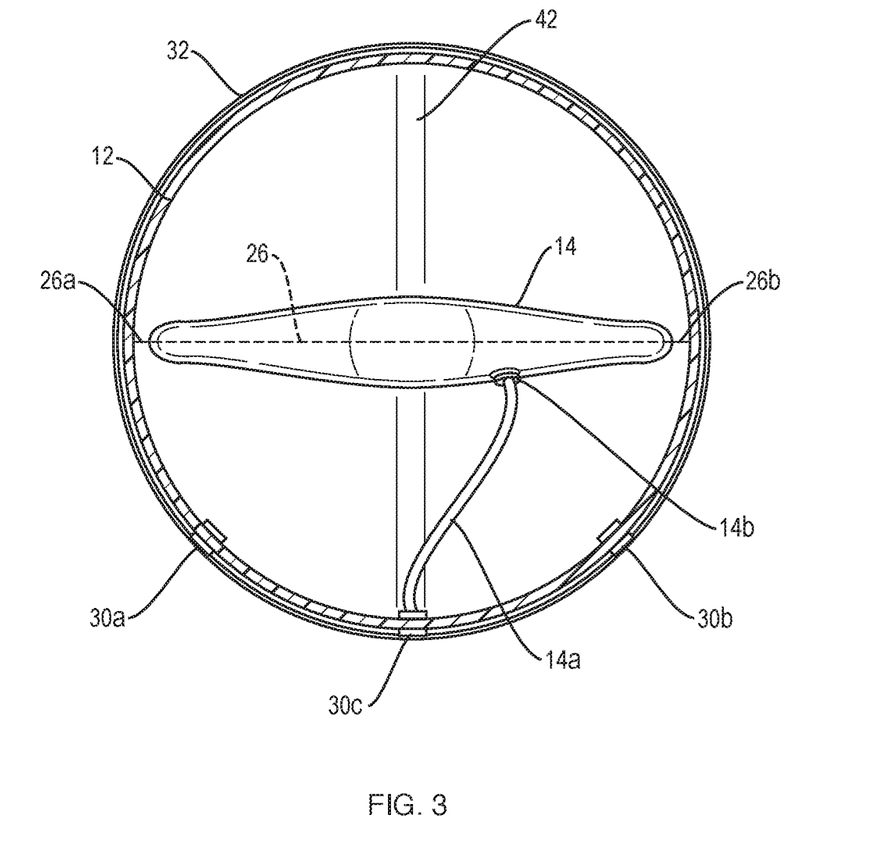
FIG. 3 is an internal view looking down from the top into the bottom of the heterotrophic bioreactor of the present invention.
Figure 4:
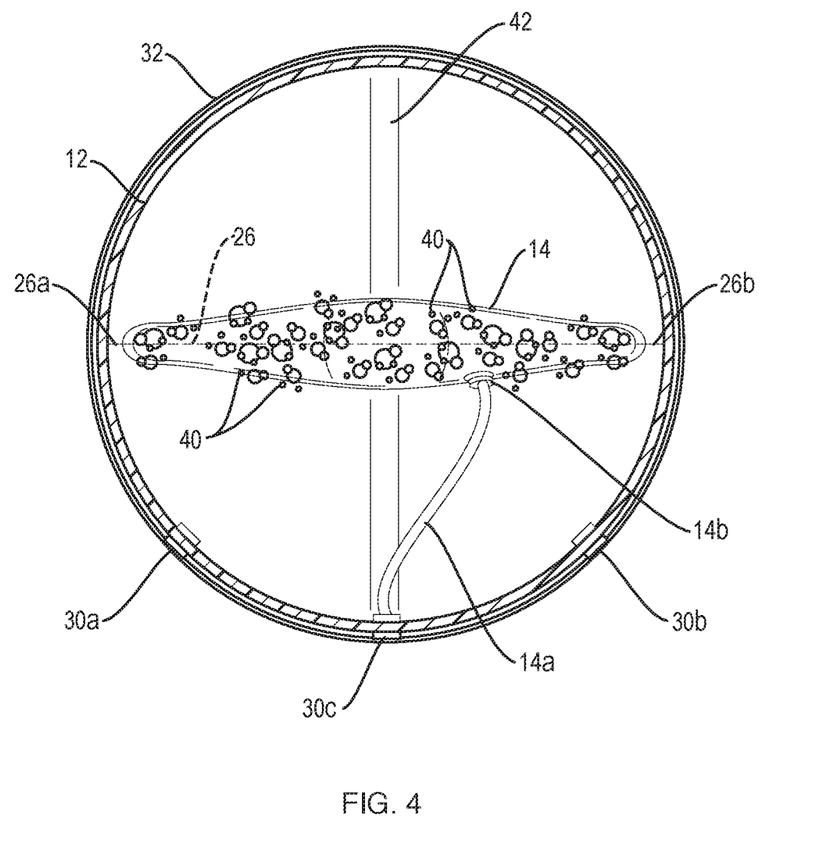
FIG. 4 is an internal view looking down from the top into the bottom of the heterotrophic bioreactor of the present invention showing bubbles exiting from the bubble diffuser.

The bubble diffuser 14 is formed of a microporous material that is capable of maintaining its structural integrity when used in the environment of plant organism growth. That is, the bubble diffuser 14 is resistant to tearing and will not degrade to the point of failure when in contact with the fluids and materials contained in the bag 12 under the processing temperatures and pressures required to complete the manufacture of desired product. It is positioned within the interior of the bag 12 at the bottom 20 and is affixed thereto at the bottom seam 26 such as by heat sealing or other means so that it remains in position at that location while pressurized with supply air passing through the bag 12 at bag port 30c through air supply tube 14a to bubble diffuser air input port 14b. The bubble diffuser 14 is made of a selectable size. In an embodiment of the invention, its size is selected so that its length extends almost from the seamed side 24 to side 28. Other size options are possible provided the bubble diffuser 14 is not so large that it becomes too buoyant within the bag 12. The bubble diffuser 14 may be a collapsible bag, a roll, a pipe or a tube having a wall or membrane that defines an interior. In one embodiment, the bubble diffuser 14 may be a roll that is about three inches in diameter when inflated as described herein. The bubble diffuser 14 includes micropores of sufficient size to enable micro bubbles 40 to pass therethrough when the interior of the bubble diffuser 14 is inflated. It is secured within the interior of the bag 12 at the bottom seam 26. When gas, such as oxygen or air, is introduced into the interior of the bag 12 through port 30c, the bubble diffuser 14 expands, inflates and is pressurized to produce the micro bubbles 40 that pass from the interior of the bubble diffuser 14 through the membrane of the bubble diffuser 14 to the interior of the bag 12. Oxygen in the gas is forced through the micropores of the bubble diffuser 14 and is thereby uniformly diffused throughout the interior of the bag 12. The size of the micropores exiting the bubble diffuser 14 is from 4 microns in diameter and larger but is not limited thereto.

The bioreactor 10 may further include an optional exhaust bag, which may be coupled to offgas outlet port 30g for venting exhaust gases produced by the reaction occurring in the bag 12 that reside in the interior of the top 16 of the bag 12. The exhaust bag may be positioned to allow condensate to return into the bag 12 through the same port 30g or it may be coupled to another coupling such as supply inlet port 30b for return of condensate to the bag 12. Optionally, an exhaust port can be made directly in the bag 12 in such a way that it forms a microporous window seamed at or near the top 16 of the bag 12. Such optional exhaust port in the form of a microporous film is seamed on to the inside surface of the bag 12. The microporous window includes pores sufficient to let offgasses of the biological reaction occurring in the interior of the bag 12 to pass there through.

All ports 30 are connected with Thermo Plastic Elastomer (TPE) tubes of which end that interfaces with either or both of the bag 12 and the bubble diffuser 14 is sealed thereto. The bag 12 as manufactured is a closed end system with gamma irradiation process to guarantee the sterilization inside of it. TPE tube can be connected to other TPE tube with sterile connector or heat sealer such as the heat sealer available from Vante Biopharm of Tucson, Ariz., or other equivalent.

The plastic bag used to make the reaction bag 12 that is cut rectangular sitting in the support 32 creates stress in parts of the bottom seam 26, and can therefore possibly tear and/or fluid within the bag 12 can ooze out. To release the stress, a wedge 42 is positioned in the support 32 under the bottom 20 of the bag 12. There are two ways to place the wedge 42 to relieve the stress. For the purpose of a preferred design, the wedge 42 is positioned so that it is at substantially 90 deg to the orientation of the bottom seam 26 so that it substantially evenly splits ends 26a and 26b as shown. The wedge 42 may be in the form of an inverted "A" frame as shown, with slightly rounded ends 42a and 42b that make contact with bottom 32a of the support 32. Other configurations of the wedge 42 are possible.

The present invention may be further described as follows:

A sterile algal growth bioreactor made with sealed plastic bag with sterile tubes connected into it in a way that all the tube fitments are aligned at one side wall of the plastic bag, and at least four tubes two of which is gas in and gas out, and two of which is liquid in and product out.

A sterile algal growth bioreactor made with sealed plastic bag with sterile tubes sealed into it in a way such that two or more of the tubes are aligned at the top of the bag on one side wall thereof and one or more of other tubes are sealed into the same side wall of the bag at other locations. At least one of the tubes is connected near the bottom for product discharge, and at least another of the tube is connected near or at the bottom for air or other gas injection.

A sterile algal growth bioreactor that is made of a plastic bag with tubes sealed into it that at least one of the tubes is connected inside such reactor into a microporous closed-end plastic bubble diffuser for the purpose of blowing gas into such microporous bubble diffuser to be used as a microbubble gas disperser inside the reactor.

The microporous bubble diffuser shall be seamed together with the outer bag at the bottom of the bag.

The microporous plastic bubble diffuser is made with a non-woven cloth with 4μ average diameter fibers.

The microporous bubble diffuser may be made of Tyvek® sheet.

A gas exhaust filter may be attached to the top port fitment. The exhaust filter may be in the form of a bag made of microporous plastic sheet material of the type used to make the microporous bubble diffuser. The exhaust bag may be smaller than the microporous bubble diffuser but preferably not smaller than 1/20 of the apparent surface area of the pillow.

A cut out window of the outer bag which is covered by heat sealed Tyvek sheet may be a substitute for the exhaust filter.

The microporous bubble diffuser may have a total apparent surface area larger than at least half the area of the cross section of the bioreactor bag, preferably as large as or larger than the cross-section area of the bag, but not exceeding the twice the surface area of the cross section of the bag.

The bubble diffuser may be seamed together with the seam of the reactor bag at the bottom of or near the bottom of the side seam.

The present invention has been described with specific examples, which are not intended to be limiting. The present invention and its equivalents are defined by the following claims.

What is claimed is:

1. A bioreactor comprising:

a plastic bag having one or more sealed seams defining an interior of the bag, one of said sealed seams being a bag bottom seam joining a front side of the bag to a rear side of the bag;

a plurality of couplings and/or ports heat sealed to the bag for insertion and removal of contents into and out of the bag;

a microbubble diffuser constructed of microporous sheet in the form of a bag or pillow with sides meeting at a diffuser bottom seam integrally formed with the bag bottom seam to contain gas within the microbubble diffuser and contain liquid in the bioreactor outside the microbubble diffuser;

a bag support surrounding and supporting the bag in an upright position when in use, the support including a wedge having a peak positioned in the support under the bottom of the bag so that the peak is substantially perpendicular to the bottom seam, wherein said wedge relieves stress on the bag bottom seam when the bioreactor is in use.

2. The bioreactor of claim 1, wherein said peak substantially evenly divides the bottom seam into portions that extend downward and away from the peak.

3. The bioreactor of claim 1, wherein said bag support is cylindrical and said wedge extends downward and laterally away from the peak to rounded ends in contact with a bottom of the bag support.

4. The bioreactor of claim 1, wherein the bottom seam separates the front side of the bioreactor from the rear side and all of said plurality of couplings and/or ports are located in one of said front side or rear side of the bioreactor.

5. The bioreactor of claim 4, wherein at least one of said plurality of couplings and/or ports is a gas inlet port coupled to the bag at or near a bottom of the bag and said bioreactor comprises a supply tube that extends from said gas inlet port to a diffuser inlet port connected to said microbubble diffuser.

6. The bioreactor of claim 5, wherein said microbubble diffuser is formed of non-woven microporous sheet heat sealed to said plastic bag at said bottom seam.

7. The bioreactor of claim 5, wherein the gas inlet port is accessible through the bag support above the wedge.

8. The bioreactor of claim 1, wherein the bioreactor is sterilized by gamma irradiation after all seams are sealed and the plurality of couplings and ports are joined to the bag and closed or plugged.

9. The bioreactor of claim 1, wherein said microporous sheet extends between the front side and the rear side of the plastic bag and the bottom seam is formed by heat sealing the front side and rear side to said microporous sheet and said microporous sheet to itself to form said bottom seam.

10. The bioreactor of claim 1, wherein said microbubble diffuser has a total apparent surface area larger than at least half the area of the cross section of the bioreactor, but not exceeding twice the surface area of the cross section of the bioreactor.

11. The bioreactor of claim 10, wherein the bioreactor has a capacity of at least 400 liters, with at least three couplings and/or ports.

12. The bioreactor of claim 1, wherein said bag support is a cylindrical cage having openings through which the plurality of couplings and/or ports are accessible from outside the bag support.

* * * * *